United States Patent [19]
Davis et al.

[11] Patent Number: 5,807,569
[45] Date of Patent: Sep. 15, 1998

[54] TOPICAL COMPOSITION

[75] Inventors: Adrian Francis Davis; Jennifer Jane Gordon, both of Weybridge, England

[73] Assignee: SmithKline Beecham p.l.c., United Kingdom

[21] Appl. No.: 443,041

[22] Filed: May 17, 1995

Related U.S. Application Data

[63] Continuation of Ser. No. 66,094, May 27, 1993, abandoned.
[51] Int. Cl.$^6$ .................................................... A61F 13/00
[52] U.S. Cl. ........................... 424/449; 424/401; 514/944
[58] Field of Search .................................... 424/449, 401; 514/944

[56] References Cited

FOREIGN PATENT DOCUMENTS 0151953  8/1985  European Pat. Off. .

*Primary Examiner*—D. Gabrielle Brouillette
*Attorney, Agent, or Firm*—Nora Stein-Fernandez; Janice E. Williams; Edward T. Lentz

[57] ABSTRACT

Two-component pharmaceutical compositions for topical application to the human or animal body and intended for mixing together on or immediately prior to application, comprising two liquid phases having different lipophilicities and a drug dissolved in at least one of the liquid phases.

25 Claims, No Drawings

TOPICAL COMPOSITION

This is a continuation of application Ser. No. 08/066,094, filed May 27, 1993, now abandoned, which is the U.S. National Phase application from PCT/GB91/02064, published Jun. 11, 1992.

The present invention relates to the topical application of active substances to the human or animal body and in particular to two-component compositions intended for mixing together either in situ on application, or immediately prior to application.

The solubility of active substances in solvent systems is important in relation to the design of topical delivery systems. It has been shown that the degree of saturation of an active substance, for example a drug, in the solvent system or vehicle is a determining factor in controlling release of the active substance.

Coldman et al.; J. Pharm. Sci., 58, 1098–1102, 1969, demonstrated that percutaneous absorption could be enhanced by over-saturating a drug solution to a supersaturated level. A supersaturated state is generated when the concentration of a solute, for example a drug, in a given solvent system exceeds the saturated solubility of the solute in that system.

Coldman prepared a solution of a drug in a mixture of a volatile and a non-volatile solvent and applied it to the surface of a sample of human skin. The volatile solvent evaporated leaving the drug in solution in the non-volatile solvent at a concentration in excess of its saturated solubility in that solvent, thereby creating a supersaturated solution in situ on the skin surface.

European Patent Publication No. 0 132 674 (EP-A-0 132 674) describes a pharmaceutical composition for generating a drug solution in a supersaturated state which is not reliant on the prior evaporation of a volatile solvent.

The composition comprises two distinct but miscible liquid phases, at least one of which contains a drug dissolved therein. The composition of the phases is such that each has a different lipophilicity (or polarity) and each confers a different saturated solubility on the drug. The composition of the liquid phases and the concentration of drug in one or both phases is such that on admixture of the two phases, the total drug concentration in the mixture thus formed is greater than the concentration of drug which a mixture of the same composition can accommodate as a saturated solution. On mixing the two liquid phases, the resulting mixture is therefore supersaturated with respect to the drug.

It is an inherent property of supersaturated solutions that they will seek to adopt a more thermodynamically stable saturated state. This will generally be achieved by precipitation of solute from the supersaturated solution. The tendency for precipitation and the time scale over which it will occur will be dependent on a number of internal and external factors, including for example the degree of saturation, the nature of solute and solvents, the presence of extraneous material and the ambient temperature.

European Patent Publication No. 0 272 045 (EP-A 0 272 045) describes a pharmaceutical composition for generating a supersaturated solution wherein the tendency for drug precipitation to occur is substantially reduced by incorporation of an antinucleating agent into at least one of the liquid phases of compositions described in EP-A 0 132 674.

It has now been found that duration of the supersaturated state, generated by certain two phase compositions in accordance with EP-A 0 132 674, is limited by solvent evaporation taking place after mixing together of the two liquid phases, for example after topical administration of the resulting supersaturated drug preparation in the form of a thin film intended for long contact time usage.

Solvent evaporation poses a particular problem with two-phase compositions as described in EP-A 0 132 674 which are formulated with a high water content.

Preferential evaporation of a more volatile solvent, such as water, after mixing of the two liquid phases has the effect of increasing the saturated solubility of the drug in the resultant mixture. An increase in drug saturated solubility is reflected in a reduction of the degree of saturation of the supersaturated drug solution.

Placebo bases with a high water content, for example hydrophilic creams and gels, are widely used in the formulation of topical preparations for delivery of topically active substances, in particular lipophilic drugs.

It has now been found that the degree of saturation in supersaturated solutions generated from pharmaceutical compositions according to EP-A 0 132 674 can be sustained by using a novel range of solvent compositions which counterbalance the deleterious effects of water loss due to evaporation.

Compositions of the present invention as hereinafter defined therefore have practical utility in the field of topical drug administration, in particular where use of thin films over long contact times is necessary or advantageous and it is desirable to maintain an enhanced level of percutaneous adsorption for an extended time period.

According to the present invention there is provided a two-phase composition for topical application, wherein the two phases are intended to be mixed together on or immediately prior to application, comprising:

a first liquid phase containing a drug dissolved therein and comprising a topically acceptable solubiliser; and a second liquid phase, physically and/or chemically different from the first phase but miscible therewith on admixture, optionally containing the same drug dissolved therein and comprising a topically acceptable carrier; the composition of the first and second liquid phases being such that each has a different lipophilicity and each confers a different saturated solubility on the drug; the concentration of drug in each phase in which it is present and the composition of each of the first and second liquid phases being such that, on admixture of the phases, the total drug concentration in the mixture thus formed is greater than the saturated drug concentration in the same mixture, whereby the said mixture is supersaturated with the drug; characterised in that the topically acceptable carrier of the second liquid phase comprises a first component which is water and a second component which has a lipophilicity intermediate between that of water and the solubiliser of the first liquid phase.

The term drug is used herein to denote topically active substances including pharmaceutically active substances and substances conferring therapeutic and/or cosmetic benefit.

The term liquid is used herein to denote materials of varying consistency ranging from lotions to viscous materials, in particular creams and gels.

It will be appreciated that compositions of the invention are not limited with respect to the physical nature of the product obtained on mixing the two liquid phases, provided that the first and second liquid phases are miscible.

The second liquid phase need not contain any drug, provided that the product obtained on admixture of the two phases is supersaturated with respect to drug. Each phase may contain one or more drugs in amounts such that the resultant product mixture is supersaturated in one or more drugs.

Preferably, a composition of the invention has a first liquid phase which is saturated with drug. More preferably, a composition of the invention has a first liquid phase which is saturated with drug and a second liquid phase which contains no drug. The degree of saturation, and hence the rate of drug release from the resulting supersaturated drug preparation after mixing, can then be readily predicted from the saturated solubility curve for a given solubiliser/carrier system.

Due to the inefficiency of percutaneous absorption, highly supersaturated systems can be of great benefit. The rate of drug penetration in situ will depend largely on the degree of saturation, vis the ratio of supersaturated drug concentration to saturated drug concentration. A degree of saturation in excess of 1 is considered useful, and values from 2, for relatively slow penetration, to 10, for rapid penetration, are preferred. By means of the present invention very high degrees of saturation may be both obtained and moreover maintained over a substantial time period.

In a composition according to the invention, the relative proportion by weight of the first liquid phase to the second liquid phase is advantageously from 1:1 to 1:12, preferably from 1:2 to 1:8.

As used herein with respect to any composition of the invention, the term solubiliser denotes a liquid in which a drug has a higher saturated solubility than in an associated carrier.

Analogously, the term carrier denotes a liquid in which a drug has a lower saturated solubility than in an associated solubiser.

Suitably a solubiliser is a liquid in which a drug is readily soluble whilst a carrier is a liquid in which a drug has poor solubility.

Since water is a necessary component of the topically acceptable carrier of the second liquid phase, it will be readily appreciated that topically acceptable solubilisers suitable for use in compositions of the present invention are generally more lipophilic or less-polar liquids. The first liquid phase may comprise more than one such liquid.

Examples of suitable solubilisers include propylene glycol, 1,3-propylene diol, polyethylene glycol, ethanol, propanol, acetone, dimethylisosorbide, dimethylsulphoxide, benzyl alcohol, and other glycol, ether and ester solvents of similar polarity.

Preferred solubilisers are propylene glycol, polyethylene glycol and ethanol.

The second component of the topically acceptable carrier of the second liquid phase is a liquid miscible with water, suitably having a lipophilicity closer to that of water than that of solubilser. Favourably the second component is not volatile at ambient, and particularly at body temperature.

Suitable liquids include glycerol and propylene glycol. A preferred liquid is glycerol.

The second component may comprise up to 50% by weight of the topically acceptable carrier, suitably from 5 to 40% by weight and preferably from 10 to 25% by weight.

In a preferred composition of the invention, the solubiliser of the first liquid phase comprises a first component which is non-volatile and a second component which is relatively more volatile at ambient, and particularly at body temperature. Favourably the second more volatile component has comparable volality to water. Suitable more volatile components include ethanol, isopropanol and acetone. A preferred more volatile component is ethanol. Suitably, a relatively more volatile second component comprises up to 50% by weight of the first liquid phase.

The invention also encompasses compositions in which a relatively more volatile solubiliser, for example ethanol, is present in the second liquid phase. The second liquid phase suitably comprises up to 20% by weight of such relatively more volatile solubiliser, for example from 4% to 20% of such relatively more volatile solubiliser.

The incorporation of a more volatile solubiliser component with comparably volatility to water, further counteracts the tendency for the degree of saturation in the supersaturated preparation, generated on mixing, to decline. Co-evaporation of this more volatile component with water further stabilises the lipophilicity (or polarity) of the resulting mixture and hence the drug saturated solubility.

Compositions of the invention may also contain an antinucleating agent. The antinucleating agent used in compositions according to the invention may be present in either or both of the said first and second liquid phases of the composition. Advantageously, it is present in at least the second phase and it may additionally be present in the first phase. In any event, when the two phases are mixed to provide a superstaturated solution, the antinucleating agent will, of course, be present in the resulting solution.

The antinucleating agent may be present in an amount of up to 10% by weight, suitably in an amount of up to 5.0% by weight, advantageously from 0.01 to 2.0% by weight, and preferably from 0.1 to 0.5% by weight, based on the total weight of the composition.

The antinucleating agent should be soluble or dispersible in the phase or phases in which it is present and, of course, in the resulting mixed solution.

Examples of suitable antinucleating agents are hydroxyalkylcelluloses, such as hydroxypropylmethylcellulose and hydroxypropylcellulose, polyvinylpyrrolidone, polyacrylic acid, and derivatives thereof. A mixture of two or more different antinucleating agents may be used. In the event that an antinucleating agent is included in each of the first and second liquid phases of the composition, the same or different antinucleating agents may be included in each phase.

The choice of suitable antinucleating agent will depend both on the particular drug and the choice of solvent materials making up the first and second phases, but suitable antinucleating agents can readily be selected by simple experiment. This may be done, for example, by preparing samples of the desired final supersaturated drug solution; adding a selection of anti-nucleating agents (in say 1% by weight concentration), one to each sample; allowing the samples to stand for say 2 hours; and noting which solutions have remained clear.

Each of the first and second liquid phases may be thickened with a suitable thickening or gelling agent of either natural or synthetic origin. Examples of thickening and gelling agents are natural gums, tragacanth, carageen, pectin, agar, alginic acid, cellulose ethers and esters, xanthan gum, guar and locust bean gum, bentonite (a collosidal hydrated aluminium silicate), veegum (colloidal magnesium aluminium silicate), laponite (a synthetic hectorite), polyvinyl alcohol, Pluronics (a Tradename), Aerosil (a Tradename colloidal silica), and Carbopol (a Tradename).

Certain thickening agents may require the addition of an adjunct which serves to activate the thickening mechanism. For example, amines are commonly used in conjunction with Carbopol suspensions.

Preservatives including anti-oxidants and UV absorbers, and other adjuvants may also be added to one or both phases.

Compositions of the invention may be prepared by processes well known in the art of pharmaceutical formulation, for example by admixture, using appropriate equipment and techniques, of the components present in each of the first and second liquid phases.

The composition of the invention may be packaged into a twin compartment pack ready for topical application by the user or patient. The user or patient would normally apply the two phases simultaneously to the treatment area and then mix the phases together in situ to create the supersaturated drug system.

The two phases may also be mixed in the pack by breaking a membrane or seal separating the first and second phases, thus creating a supersaturated solution in the pack, prior to application. Suitable packs for such purposes are commercially available.

Compositions of the invention are suitable for any medical, cosmetic or other treatment of the body surface, including the skin, scalp, nails and oral mucosa. Compositions of the invention may also be of value in delivering drugs to the systemic system by the so-called transdermal route, in which a drug is applied topically for absorption through the skin for systemic therapy.

Compositions of the invention provide a means by which many drugs which exhibit poor topical absorption, or which are required at high dosage levels, can be administered effectively in a transdermal system. Accordingly, the invention, provides a transdermal device containing a composition according to the invention.

Since a composition of the invention consists of two distinct phases, such a device will suitably comprise two compartments, for separate storage of the two phase divided by a breakable seal or membrane to allow for mixing of the two phases prior to the attachment of the device to the skin surface.

In a further aspect of the invention there is provided a method for topical treatment of the human or animal body which comprises applying thereto an effective amount a pharmaceutical composition according to the invention.

Suitable drugs for use in the composition and method of the invention are many and varied and include agents having the following activities:

anti-pruritics, anti-bacterials, anti-septics, anti-virals, anti-fungals, anti-psoriasis agents, anti-acne agents, anti-dandruff agents; anti-histamines, local anaesthetics, analgesics, anti-inflammatories, anti-plaque agents, beta-adrenoceptor blockers, broncho-spasm relaxants, anti-angina agents, anti-travel sickness agents, decongestants, anti-tussives, anti-coagulants, head-lice treatments, anti-baldness treatments, and substances which have a beneficial effect on the skin for example in the treatment of photoageing and UV-damaged skin.

Suitable drug types include, for example, steroids, non-steroidal anti-inflammatory agents, imidazoles and retinoids, for example all-trans retinoic acid (tretinoin), 13-cis retinoic acid (isotretinoin) and retinyl esters such as retinyl propionate.

The following Examples illustrate the invention. They provide two-phase formulations which on mixing the two phases generate supersaturated solutions.

In each of Examples 1,2,5,6,7,8,9 and 10 a supersaturated solution is formed by mixing one part of the first phase with seven parts of the second phase. In Examples 3 and 4, a supersaturated solution is formed by mixing one part of the first phase with four parts of the second phase.

In addition to the constituents described in the Examples, the first and second phases may each contain, as appropriate and where not already indicated, adjuvants such as anti-nucleating agents, for example HPC, HPMC and PVP; antioxidants, for example butylated hydroxyanisole; preservatives, for example phenoxytol; gelling or thickening agents, for example Carbopol 980 with a suitable neutralising agent such as trisamino for a non-aqueous phase or sodium hydroxide for an aqueous phase; and UV absorbers, for example benzophenone-3.

The following abbreviations are used:
PEG: polyethylene glycol
PVP: polyvinylpyrrolidone
HPMC: hydroxypropylmethylcellulose
HPC: hydroxypropylcellulose

|  |  | % w/w |
|---|---|---|
| *Example 1* | | |
| First Phase: | Hydrocortisone Acetate | 0.20 |
|  | Propylene Glycol | 49.40 |
|  | PEG 400 | 49.40 |
|  | PVP | 1.00 |
| Second Phase: | HPMC | 0.50 |
|  | Glycerol | 38.00 |
|  | Water | 61.50 |
| *Example 2* | | |
| First Phase: | Hydrocortisone Acetate | 0.16 |
|  | PEG 400 | 99.84 |
| Second Phase: | Glycerol | 20.00 |
|  | Water | 80.00 |
| *Example 3* | | |
| First Phase: | Indomethacin | 0.25 |
|  | Propylene glycol | 99.75 |
| Second Phase: | Glycerol | 40.00 |
|  | Water | 60.00 |
| *Example 4* | | |
| First Phase: | Retinyl Propionate | 0.01 |
|  | PEG 400 | 99.99 |
| Second Phase: | Propylene Glycol | 40.00 |
|  | Water | 60.00 |
| *Example 5* | | |
| First Phase: | Hydrocortisone Acetate | 0.20 |
|  | Propylene Glycol | 49.40 |
|  | Ethanol | 49.40 |
|  | PVP | 1.00 |
| Second Phase: | HPMC | 0.50 |
|  | Glycerol | 38.00 |
|  | Water | 61.50 |
| *Example 6* | | |
| First Phase: | Hydrocortisone Acetate | 0.20 |
|  | Propylene Glycol | 49.40 |
|  | Ethanol | 49.40 |
|  | PVP | 1.00 |
| Second Phase: | HPMC | 0.50 |
|  | Glycerol | 19.00 |
|  | Water | 80.50 |
| *Example 7* | | |
| First Phase: | Hydrocortisone Acetate | 0.16 |
|  | PEG 400 | 99.84 |
| Second Phase: | Glycerol | 17.00 |
|  | Water | 68.50 |
|  | Ethanol | 14.50 |
| *Example 8* | | |
| First Phase: | Retinoic Acid | 0.02 |
|  | Propylene Glycol | 99.98 |
| Second Phase: | Glycerol | 12.00 |
|  | Water | 72.00 |
|  | Ethanol | 16.00 |
| *Example 9* | | |
| First Phase: | Hydrocortisone Acetate | 0.20 |
|  | Ethanol | 99.80 |
| Second Phase: | HPMC | 0.50 |
|  | Glycerol | 19.00 |
|  | Water | 80.50 |

-continued

|  |  | % w/w |
| --- | --- | --- |
| Example 10 | | |
| First Phase: | Retinoic Acid | 0.02 |
|  | HPC | 1.00 |
|  | PEG 400 | 98.98 |
| Second Phase: | Glycerol | 5.80 |
|  | Ethanol | 15.50 |
|  | Propylene Glycol | 3.80 |
|  | HPMC | 1.00 |
|  | Water | 73.90 |

We claim:

1. In a two-phase composition for topical application, wherein the two phases are intended to be mixed together on or immediately prior to application, comprising:
   a. a first liquid phase containing a drug dissolved therein and comprising a topically acceptable solubiliser; and
   b. a second liquid phase, physically and/or chemically different from the first phase but miscible therewith on admixture, with or without the same drug dissolved therein and comprising a topically acceptable carrier; and
   c. wherein the composition of each of the first and second liquid phases has a different lipophilicity and each phase confers a different saturated solubility on the drug; wherein upon admixture of the phases, the resultant mixture is supersaturated with the drug; the improvement in said two-phase composition is that the topically acceptable carrier of the second liquid phase comprises a first component which is water and 5–40% by weight of a second liquid component which has a lipophilicity intermediate between that of water and the solubiliser of the first liquid phase, thus sustaining the supersaturated drug mixture.

2. A composition as claimed in claim 1 in which the topically acceptable solubiliser is selected from the group consisting of propylene glycol, 1,3-propylene diol, polyethylene glycol, ethanol, propanol, acetone, dimethylisosorbide, dimethylsulphoxide, and benzyl alcohol.

3. A composition as claimed in claim 2 in which the solubiliser is propylene glycol, polyethylene glycol, ethanol or mixtures thereof.

4. A composition as claimed in claim 1 in which the second component of the topically acceptable carrier is glycerol or propylene glycol.

5. A composition as claimed in claim 1 in which the second liquid phase comprises up to 20% by weight of a relatively more volatile second component.

6. A composition as claimed in claim 1 in which the first liquid phase is saturated with drug.

7. A composition as claimed in claim 1 in which the relative proportion by weight of the first liquid phase to the second liquid phase is from 1:1 to 1:12.

8. A composition as claimed in claim 1 in which the degree of saturation on admixture of the first and second liquid phases is in the range 2 to 10.

9. A composition as claimed in claim 1 in which the drug is a steroid, a non-steroidal anti-inflammatory agent, an imidazole or a retinoid.

10. A twin compartment pack containing a composition as defined in claim 1, the first liquid phase being in one compartment and the second liquid phase being in the other compartment.

11. A transdermal device containing a composition as defined in claim 1.

12. A method for topical treatment of the human or animal body which comprises applying thereto an effective amount of a pharmaceutical composition as defined in claim 1.

13. In a two-phase composition for topical application, wherein the two phases are intended to be mixed together on or immediately prior to application, comprising:
    a. a first liquid phase containing a drug dissolved therein and comprising a topically acceptable solubiliser; and
    b. a second liquid phase, physically and/or chemically different from the first phase but miscible therewith on admixture, with or without the same drug dissolved therein and comprising a topically acceptable carrier; and
    c. wherein the composition of each of the first and second liquid phases has a different lipophilicity and each phase confers a different saturated solubility on the drug; wherein upon admixture of the phases, the resultant mixture is supersaturated with the drug; the improvement in said two-phase composition is that the topically acceptable carrier of the second liquid phase comprises a first component which is water and a second liquid component which has a lipophilicity intermediate between that of water and the solubiliser of the first liquid phase, and the topically acceptable carrier of the first liquid phase comprises a first component which is non-volatile and a relatively more volatile second component thus further sustaining the supersaturated drug mixture.

14. A composition as claimed in claim 13 in which the relatively more volatile second component has comparable volatility to water.

15. A composition as claimed in claim 14 in which the relatively more volatile second component comprises up to 50% by weight of the first liquid phase.

16. A composition as claimed in claim 14 in which the relatively more volatile second component is ethanol, isopropanol or acetone.

17. A composition as claimed in claim 13 in which the first liquid phase is saturated with drug.

18. A composition as claimed in claim 13 in which the relative proportion by weight of the first liquid phase to the second liquid phase is from 1:1 to 1:12.

19. A composition as claimed in claim 13 in which the degree of saturation on admixture of the first and second liquid phases is in the range 2 to 10.

20. A composition as claimed in claim 13 in which the drug is a steroid, a non-steroidal anti-inflammatory agent, an imidazole or a retinoid.

21. A composition as claimed in claim 13 in which the second liquid phase comprises up to 20% by weight of a relatively more volatile second component.

22. A twin compartment pack containing a composition as defined in claim 13, the first liquid phase being in one compartment and the second liquid phase being in the other compartment.

23. A transdermal device containing a composition as defined in claim 13.

24. A method for topical treatment of the human or animal body which comprises applying thereto an effective amount of a pharmaceutical composition as defined in claim 13.

25. In a two-phase composition for topical application, wherein the two phases are intended to be mixed together on or immediately prior to application, comprising:
    a. a first liquid phase containing a drug dissolved therein and comprising a topically acceptable solubiliser; and
    b. a second liquid phase, physically and/or chemically different from the first phase but miscible therewith on admixture, with or without the same drug dissolved therein and comprising a topically acceptable carrier; and c. wherein the composition of each of the first and second liquid phases has a different lipophilicity and each phase confers a different saturated solubility on the drug; wherein upon admixture of the phases, the resultant mixture is supersaturated with the drug; the improvement in said two-phase composition is that the topically acceptable carrier of the second liquid phase comprises a first component which is water and 10–25% by weight of a second liquid component which has a lipophilicity intermediate between that of water and the solubiliser of the first liquid phase, thus sustaining the supersaturated drug mixture.

* * * * *